United States Patent
Okubo et al.

(10) Patent No.: US 7,670,857 B2
(45) Date of Patent: Mar. 2, 2010

(54) INSPECTION METHOD, MANUFACTURING METHOD OF PIECE FOR ANALYSIS, ANALYSIS METHOD, ANALYZER, MANUFACTURING METHOD OF SOI WAFER, AND SOI WAFER

(75) Inventors: Akira Okubo, Tokyo (JP); Hideyuki Kondo, Tokyo (JP)

(73) Assignee: Sumco Corporation, Tokyo (JP)

( * ) Notice: Subject to any disclaimer, the term of this patent is extended or adjusted under 35 U.S.C. 154(b) by 958 days.

(21) Appl. No.: 10/544,178

(22) PCT Filed: Oct. 16, 2003

(86) PCT No.: PCT/JP03/13271
§ 371 (c)(1),
(2), (4) Date: Apr. 24, 2006

(87) PCT Pub. No.: WO2004/070828
PCT Pub. Date: Aug. 19, 2004

(65) Prior Publication Data
US 2006/0249479 A1 Nov. 9, 2006

(30) Foreign Application Priority Data
Feb. 3, 2003 (JP) .............................. 2003-026540

(51) Int. Cl.
*H01J 37/28* (2006.01)
*G01L 21/30* (2006.01)
(52) U.S. Cl. ......................................... 438/14; 216/59
(58) Field of Classification Search ............. 438/14–18; 216/59; 250/306, 307, 309; 324/71.5; 374/57
See application file for complete search history.

(56) References Cited

U.S. PATENT DOCUMENTS 5,770,861 A 6/1998 Hirose et al.
2002/0022348 A1* 2/2002 Sakaguchi et al. .......... 438/480

FOREIGN PATENT DOCUMENTS

EP 0 738 004 A1 10/1996

(Continued)

OTHER PUBLICATIONS

"Saishin Kotai Hyomen/Bisho Ryoiki no Kaiseki Hyoka Gijutsu, (Recent technologies for analysis and evaluation of solid surface and minute region," Riaraizu Sha, Mar. 31, 1991, pp. 95-104; particularly, pp. 100-103.

(Continued)

*Primary Examiner*—Victor A Mandala
*Assistant Examiner*—Whitney Moore
(74) *Attorney, Agent, or Firm*—Pillsbury Winthrop Shaw Pittman, LLP (57) ABSTRACT

An inspection method is provided for accurate measurement of conductive materials as defects within a silicon oxide film base material embedded in a SOI wafer sample. In the method, the internal state of a sample 2 is inspected by measuring an conductive material within an insulating base material 11 formed upon the sample 2. Ions or electrons are irradiated upon the surface of the inspection region of the base material 11. A surface image is imaged with secondary electrons emitted from the surface 11a and the vicinity of the surface. The inspection region is etched and a surface image is imaged successively with secondary electrons emitted from a surface 11b and from its vicinity, renewed successively at the etched depth. The conductive material within the base material 11 is measured based upon the accumulated surface images.

7 Claims, 7 Drawing Sheets

FOREIGN PATENT DOCUMENTS

| JP | 6-96712 A | 4/1994 |
|----|-----------|--------|
| JP | 11-074493 | 3/1999 |
| JP | 11-87450 | 3/1999 |
| JP | 2000-031225 | 1/2000 |
| JP | 2000-329716 A | 11/2000 |
| JP | 2001-174421 A | 6/2001 |
| JP | 2001-319954 | 11/2001 |

OTHER PUBLICATIONS

International Search Report for International Application No. PCT/JP03/13271 dated Feb. 3, 2004.

Chinese Office Action for Chinese Patent Application No. 200380109405.9 dated Jun. 6, 2008.

Japanese Office Action for Japanese Application No. 2004-567897 dated Apr. 7, 2009.

Kunio Takayanagi et al., "Semiconductor Measurement Evaluation Dictionary", Japan Science Forum Corporation, Sep. 12, 1997, pp. 87-90.

Notice of Reasons for Rejection for Japanese Application No. 2004-567897 dated Nov. 4, 2009.

Inkon B J et al.: "Subsurface nanoindentation deformation of Cu-Al multilayers mapped in 3D by focused ion beam microscopy," Journal of Microscopy, vol. 201, pt. 2, Feb. 2001, pp. 256-269.

Dunn D N et al.: "Reconstruction of three-dimensional chemistry and geometry using focused ion beam microscopy, "Applied Science Letters, vol. 75, No. 21, Nov. 22, 1999, pp. 3414-3416.

Sakamoto T. et al.: "Development of an ion and electron dual focused beam apparatus for three-dimensional microanalysis," Japanese Journal of Applied Physics, vol. 37, no. 4A, Apr. 1998, pp. 2051-2056.

Supplementary European Search Report for European EP 03 75 6661 dated Dec. 17, 2009.

\* cited by examiner

INSPECTION METHOD, MANUFACTURING METHOD OF PIECE FOR ANALYSIS, ANALYSIS METHOD, ANALYZER, MANUFACTURING METHOD OF SOI WAFER, AND SOI WAFER

CROSS-REFERENCE TO RELATED APPLICATIONS

This application is the U.S. National Stage of International Application No. PCT/JP2003/013271, filed Oct. 16, 2003, which relies for priority upon Japanese Patent Application No. 2003-026540, filed Feb. 3, 2003, the contents of both of which are incorporated herein by reference in their entireties.

TECHNICAL FIELD

The present invention relates to an inspection method of the internal state of a sample, by measuring conductive materials included within the sample of insulating base material or the like, and to an inspection method which measures defects within a silicon oxide layer embedded in a SOI wafer; and also relates to a manufacturing method of a piece for analysis, an analysis method, an analyzer based upon this inspection method, and a manufacturing method of a SOI wafer, and a SOI wafer.

BACKGROUND ART

Generally, a SOI (Silicon On Insulator) wafer with a single crystal silicon (Si) thin film (a SOI layer) upon an insulating silicon oxide ($SiO_2$) layer (a BOX layer) provides high withstand voltage, since a substrate (the sample subjected to inspection) and the SOI layer, which is the device manufacturing layer, are electrically separated from one another; and the SOI wafer has features that the parasitic capacitance is low, and that, along with the anti radiation capability being great, there is no substrate bias effect. Therefore, beneficial effects such as high speed performance, low electrical power consumption, soft error free and the like are anticipated, and as substrates for next generation elements, various developments are being undertaken.

As a representative manufacturing method for a SOI wafer, there are so called bonding wafer technology and a SIMOX (Separation by IMplanted OXygen) technology. The bonding wafer technology forms an oxidized layer upon one or both of two wafers, and adhere the two wafers together intervening the oxide layer, in which the bonding is performed by heat processing the mechanically clamped wafers, and the SOI layer is manufactured by a mirror finish of the bond wafers by grinding and polishing. Since the crystallinity of the SOI layer made by the bonding is equal to that of the bulk silicon wafer, problems of defects and the like are few, and devices formed on the SOI layers have an excellent characteristics.

As a method for evaluating the defect density and the like within the SOI layer of the SOI wafer, there are proposed a method of washing the SOI wafer with an alkali detergent and dipping it into a solution of hydrofluoric acid to enlarge the etch pits due to the defects, and making the evaluation by measurement (for example, refer to Patent Reference No. 1), and a method of, after binding a SOI substrate and a bulk Si wafer, leaving only the surface Si layer upon the side of the bulk Si wafer, then etching the bulk Si wafer from the side of the surface Si layer using a selective etching liquid, and actualizing crystal defects and evaluating them (for example, refer to Patent Reference No. 2), and the like.

Furthermore, in a SIMOX technology, by oxygen ion implantation into a silicon substrate and high temperature heat processing within an Ar (argon)/$O_2$ (oxygen) gas atmosphere, an oxygen super saturated region is converted into a BOX layer ($SiO_2$ is formed by the oxygen ions being implanted into the Si), and SOI layer remains on the BOX layer, then forms a SOI wafer (a SIMOX wafer). In the SIMOX technology, since grinding and polishing as in the bonding wafer technology are not required, a benefit of comparatively simple manufacturing process is obtained.

However, in the SIMOX technology, there is a problem that during formation of the BOX layer within the silicon substrate by high temperature heat processing, a large number of defects are generated as Si parts which are not oxidized escaping from oxygen implantation. As a method of evaluating density of such defects in a BOX layer, an evaluation method is proposed (for example, refer to Patent Reference No. 3), in which, after eliminating the heat oxidized layer with HF liquid, SOI layer is etched with TMAH liquid and the defects within the BOX layer are etched to form etch pits, these etch pits are measured.

A method for defect analysis is known, in which a piece for analysis with a thin film shape is prepared from any part including the BOX layer, and by TEM (transmission electron microscope) observation of the piece, shape and types of defects are analyzed.

The following references are cited by way of example:
Patent Reference No. 1: Japanese Unexamined Patent Application, First Publication No. H11-74493 (FIG. 3)
Patent Reference No. 2: Japanese Unexamined Patent Application, First Publication No. H11-87450 (FIG. 1)
Patent Reference No. 3: Japanese Unexamined Patent Application, First Publication No. 2000-31225 (FIG. 1)

However, in an inspection of a SIMOX wafer by the above described method for defect evaluation, since the defects are measured not directly, but indirectly by measuring etch pits originating from the defects, there is a problem in the accuracy of inspection. Moreover, since only those defects are etched which penetrate the BOX layer or contact with the SOI layer, defects positioned within the BOX layer are not etched and cannot be measured. In other words, since the defects distributing three dimensionally within the BOX layer escape from measurement, the accuracy of inspection is deteriorated.

In the above described method of analyzing defects, there is a problem that, since the piece for analysis is processed from any part of the BOX layer, when the defect density is high, the piece for analysis include defects in high probability, but when the defect density is low, the probability that the piece for analysis includes defects is low, and analysis of the defects based on observation of such piece for analysis is remarkably low in efficiency. In the prior art, due to the fact that accurate inspection of the defects has been impossible, or efficient analysis has been impossible, it has been difficult to specify manufacturing conditions for reducing production of defects, and it has been impossible to manufacture a SIMOX wafer of high quality with few defects. As well in a SOI wafer made by a bonding wafer technology, a method of accurate evaluation of defects has not been established.

DISCLOSURE OF INVENTION

The present invention has been conceived in the light of the above described problems, and its object is to provide an inspection method which can accurately measure defects (conductive materials) within a silicon oxide layer (a base material) embedded in a SOI wafer (a sample subjected to inspection); a manufacturing method of a piece for analysis, and a method of analyzing defects and a defect analyzer which take advantage of the inspection method; and a method for manufacturing a SIMOX wafer of high quality with few defects, and such a SIMOX wafer.

In order to solve the above described problems, the invention proposes the following means.

The inspection method according to the present invention is an inspection method of the internal state of a sample, by measuring conductive materials included within the sample of insulating base material, wherein by irradiating ions or electrons to the surface for inspection, a surface image of secondary electron emitted from said surface and its vicinity is imaged, by etching said surface and from an underlying surface renewed successively at the etched depth, a surface image of secondary electron emitted from the underlying surface and its vicinity is imaged successively, and said conductive material within said base material is measured based upon accumulated said surface images, and an internal state of said sample is inspected.

In the inspection method of the invention, by irradiating ions or electrons to the surface for inspection, a surface image of secondary electron emitted from said surface and its vicinity is imaged, by etching said surface and from an underlying surface renewed successively at the etched depth, a surface image of secondary electron emitted from the underlying surface and its vicinity is imaged successively, and said conductive material within said base material is measured based upon said surface images successively accumulated for each depth datum, and the internal state of said sample is inspected, accordingly in the successive imaging of surface images, secondary electron images are imaged intermittently at each etched depth interval, i.e. not continually in the depth direction. In other words, direct measurement of the conductive material positioned in the interior of the insulating base material is enabled. By this method, it is possible to inspect the internal state of the sample accurately. Furthermore, it is possible to obtain a result of inspection of desired accuracy by controlling the depth interval (etching rate).

The inspection method according to the invention is the above described inspection method wherein said etching is performed with an ion beam, and said etching and said imaging of surface image are performed at the same time.

In the inspection method of the invention, the surface etching is performed with an ion beam, and the etching and the imaging of said surface image are performed at the same time. In other words, the surface image is imaged by detecting the secondary electron emission caused by the ion beam for the etching. Therefore, the sample is inspected without shifting the sample between the etching and imaging the surface image. By this method, along with shortening a time for the inspection, it is possible to obtain an accurate result of inspection, by inspecting the sample regularly immobilized during the inspection.

Furthermore, the inspection method according to the invention is the above described inspection method, wherein preferably said sample is a SOI wafer, said base material is an embedded silicon oxide layer, and said conducting material is a defect.

In the method of the invention, since the sample is a SOI wafer, the base material is an embedded silicon oxide layer, and the conductive material is a defect, measurement is performed for the conducting defects within the embedded silicon oxide layer which is the insulating layer of the SOI wafer. This method enables direct measurement of defects which were measured indirectly in the prior art. Furthermore, it is possible to measure three dimensionally defects in the interior of the silicon oxide layer, which in the prior art could not be measured. Accordingly, it is possible to inspect a SOI wafer more accurately than in the prior art.

The inspection method according to the present invention is the above described inspection method, wherein preferably said sample is a SOI wafer manufactured by the SIMOX technology.

Since, in the inspection method of the invention, the sample is a SOI wafer manufactured by the SIMOX technology, defects generated in large numbers in the interior of an embedded silicon oxide layer of a SIMOX wafer are measured accurately, and the accuracy of inspection of a SIMOX wafer is enhanced.

The manufacturing method of a piece for analysis according to the invention is a manufacturing method of a piece for analysis using any one of the methods of inspection described above, wherein said conductive material within said base material is specified based on said surface image; to form a thin film of analysis region including at least a portion of said specified conductive material, said base material other than the analysis region is etched away leaving said base material of said analysis region in the depth direction; and thereby a piece for analysis including said analysis region is manufactured.

In the manufacturing method of a piece for analysis according to this invention, a conductive material within said base material is specified based on said surface image, so that an analysis region of a thin film shape of a predetermined thickness is formed which includes at least a portion of the specified conductive material; and leaving the base material of said analysis region in the depth direction, the base material other than the analysis region is etched away, and thereby a piece for analysis including said analysis region is manufactured. Therefore a piece for analysis is manufactured reliably including at least a portion of a conductive material in the interior of the analysis region. In other words, since the prior art made analysis region without specifying the position of conductive material, it was impossible to ensure a presence of conductive material within the analysis region; but, by forming the analysis region after specifying the conductive material using the above described method, a piece for analysis is manufactured in which an conductive material is reliably included within the analysis region. Furthermore, by forming the analysis region with the ion beam used in the above described inspection method, the same apparatus can be used for the inspection and manufacture of the piece for analysis, so that, along with being able to inspect the sample and to manufacture of the piece for analysis in a series of operation within a short time, also it is possible more reliably to ensure that the specified conductive material is included within the piece for analysis. By this method, it is possible to reduce the manufacturing cost of the piece for analysis, and enhance the manufacturing efficiency for the piece for analysis.

The analysis method according to the invention is an analysis method using a piece for analysis manufactured by the manufacturing method described above, wherein a state of said conductive material is analyzed by the observation of said conductive material included in said piece for analysis.

In the analysis method of the invention, since a state of the conductive material is analyzed by the observation of conductive material included in the piece for analysis, it is possible to observe the conductive material reliably, analyze the state of the conductive material efficiently. For example, by forming the thickness of thin film constituting the region for analysis of the piece for analysis to be not more than 0.5 μm, and observing the film with TEM image, the shape and the type of the conductive material is analyzed.

The analysis method according to the invention is an analysis method using any one of the methods of inspection described above, wherein three dimensional distribution of said conductive material is analyzed from accumulated said surface images.

In the analysis method of the invention, since the three dimensional distribution of said conductive material is analyzed from accumulated said surface images, it is possible to specify the parts tending to generate the conductive materials in a three dimensional manner. For example, it is possible to analyze whether the production of defects is caused by a shortage of implantation of oxygen ions, or the like, based on the three dimensional distribution of the defects within the embedded silicon oxide layer of a SIMOX wafer.

The analyzer according to the invention is an apparatus for analysis used for the above described method for analysis, comprising: a stage upon which said sample is mounted; an ion source which produces an ion beam which is irradiated; upon said sample; a beam control device for focusing and scanning the ion beam; a secondary electron detector which detects secondary electrons emitted from said sample; a control system which controls the ion source and the beam control device; a imaging system which images the result of detection by said secondary electron detector as said surface image; and an analyzing device which analyzes the three dimensional distribution of said conductive material from accumulated said surface images.

Since, the analyzer of the invention comprises a stage upon which said sample is mounted; an ion source which produces an ion beam which is irradiated upon the sample; a beam control device for focusing and scanning the ion beam; a secondary electron detector which detects secondary electrons emitted from the sample; a control system which controls the ion source and the beam control device; a imaging system which images the result of detection by said secondary electron detector as said surface image; and an analyzing device which analyzes the three dimensional distribution of the conductive material from accumulated said surface images, three dimensional distribution of the conductive material is analyzed by the analyzing device. For example, by using a conventional imaging system for two dimensional surface images, accumulating surface images successively renewed at the etched depth, and providing an analyzing device which analyzes the three dimensional distribution from the accumulated surface images, it is possible to analyze the three dimensional distribution.

The manufacturing method of a SOI wafer according to the invention is a manufacturing method of a SOI wafer using the above described analysis method, wherein the SOI wafer is manufactured under manufacturing conditions specified by feeding back the state of said conductive material or its three dimensional distribution which has been analyzed.

In the manufacturing method of a SOI wafer of the invention, since the SOI wafer is manufactured under manufacturing conditions specified by feeding back the state of said conductive material or its three dimensional distribution which has been analyzed, it is possible to specify the manufacturing conditions in which the number of the conductive materials is reduced, by analyzing the samples manufactured in different conditions accurately and with good efficiency. By this method, it is possible to manufacture a SOI wafer in which only a small number of defects is included within the embedded silicon oxide layer.

Here, as parameters for the manufacturing conditions which are fed back, it is possible to apply: as conditions for implantation of the oxygen ions into the silicon wafer during the oxygen implantation process, the implantation energy, the dosage of oxygen ions, and the temperature of the wafer during dosage; and, furthermore, the heat process, the oxidization process, after the oxygen implantation process, and the temperature elevation speed, the heat processing temperature, the time of maintenance during the heat processing, the temperature lowering speed, and the oxygen partial pressure ratio during the annealing process.

Since the SOI wafer according to the present invention is manufactured by the manufacturing method of a SOI wafer described above, the defects are few in number and the product quality is high, and it excels in various characteristics.

BEST MODE FOR CARRYING OUT THE INVENTION

In the following, embodiments of this invention will be explained with reference to the drawings.

Figure 1:
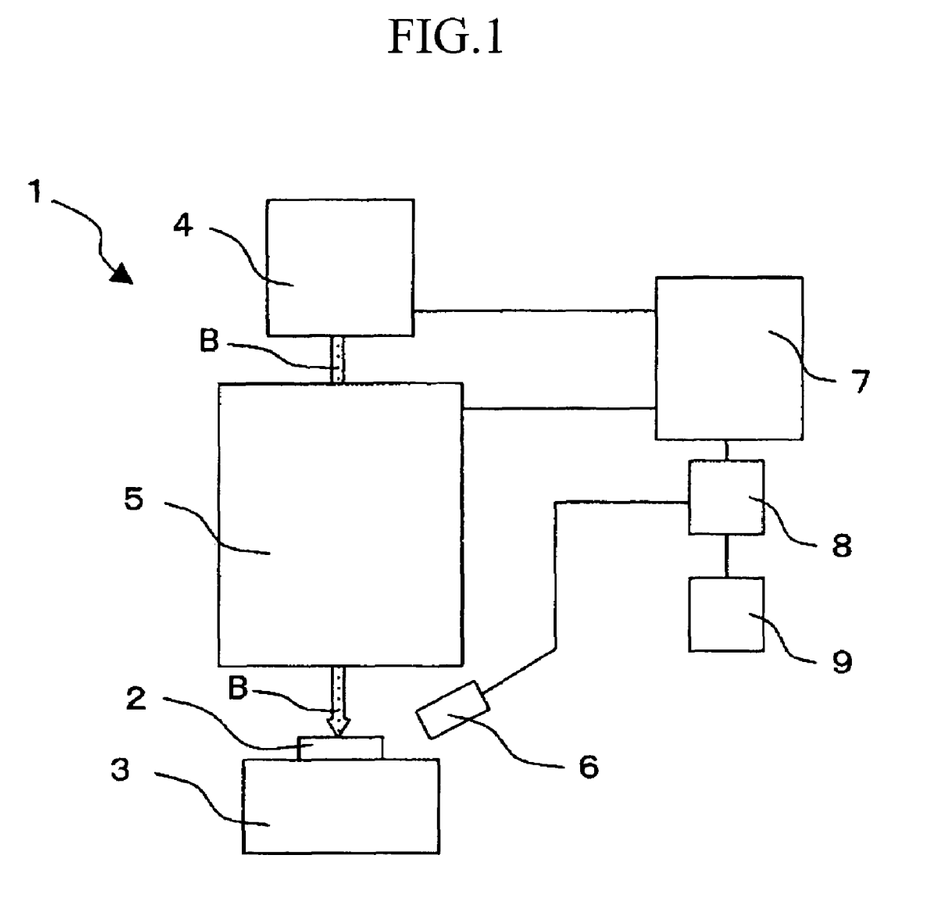
FIG. 1 is a schematic structural of a FIB apparatus which is used in an inspection method according to an embodiment of the present invention.

FIG. 1 is a schematic structural of a FIB (focused ion beam) apparatus which inspects a substrate sample (an element subjected to inspection), and this FIB apparatus is used in SIM (scanning ion microscope) imaging, preparation of a TEM sample, or rectification of defect in a photo-mask, or the like. The FIB apparatus 1 comprises a sample stage 3 upon which a substrate sample 2 is mounted, an ion source 4 which generates an ion beam B which is irradiated upon the substrate sample 2, a beam control device for focusing and scanning the ion beam B, a secondary electron detector 6 which detects secondary electrons emitted from the substrate sample 2, a control system 7 which controls the ion source 4 and the beam control device 5, a imaging system 8 which images the detection results of the secondary electron detector as a surface image, and an analyzing device 9 which analyzes a three dimensional distribution of conductive materials from the accumulated surface images. The beam control device 5 comprises a condenser lens and an XY deflector and so on, and is a device which controls the focusing point of the ion beam B in the Z direction of the substrate sample 2, and controls scanning of the measurement region of the ion beam B in the X and Y directions.

Figure 2A:
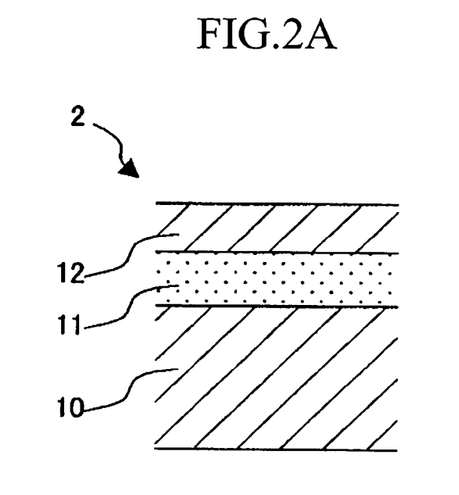
FIG. 2A is an explanatory figure schematically showing a situation during inspection of a sample.
Figure 2B:
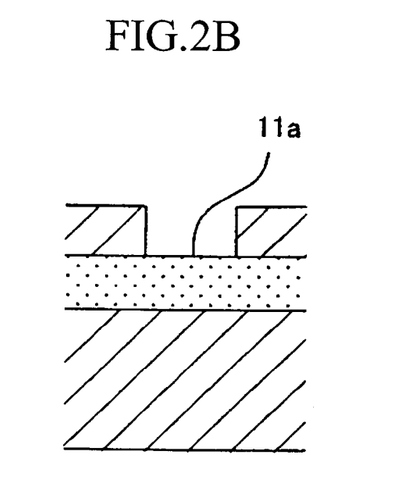
FIG. 2B is an explanatory figure schematically showing a situation during inspection of a sample.

Inspection of a substrate sample 2 with a FIB apparatus 1 as described above is performed in a chamber of a vacuum not more than about 104 Pa, and, as the ion beam B, Ga+ ions are used. As the substrate sample 2, a SOI wafer manufactured by a bonding wafer technology or a SIMOX technology or the like is used, and a BOX layer (an embedded silicon oxide layer) 11 is formed upon the upper surface of a silicon substrate 10 like the one shown in FIG. 2A, and a SOI layer (a silicon single crystal thin layer) 12 is formed upon the upper surface of the BOX layer 11. The substrate sample is mounted upon the sample stage 3 with the SOI layer 12 facing upwards, and, in a step before the inspection, the SOI layer on the upper surface of the portion for inspection of the BOX layer 11 is removed as shown in FIG. 2B, so that the surface 11a of the BOX layer 11 is exposed.

In the inspection of the substrate sample 2, the ion beam B irradiated towards the substrate sample 2 from the ion source 4 is controlled by the beam control device 5, and the surface 11a of the BOX layer 11 is etched with the ion beam B. At this time, the etching rate of the BOX layer 11 which is being etched, in other words the amount of etching per time, is determined by the acceleration voltage and the current density of the ion beam B, and for example, where the acceleration voltage is 30 keV, the ion beam current value is 320 pA, and the ion beam diameter is 54 nm, etching is performed at an etching rate of about 15 nm/min. And the secondary electrons emitted from the BOX layer 11 during etching are detected by the secondary electron detector 6.

At this time, since the number of secondary electrons emitted from the silicon (the conductive materials) is greater than that emitted from the silicon oxide layer (the base material), the defects which are present in the BOX layer 11 (lumps of silicon which are interspersed as islands which have not been oxidized, hereinafter termed silicon islands) are measured. In other words, the results of detection from the secondary electron detector 6 form a SIM image (a surface image) by the imaging system 8, and a SIM image is imaged as though the silicon islands are shining in the interior of the dark BOX layer 11. The resolution of the SIM image at this time is determined by the current of the ion beam B, and in the case of, for example, 80 pA, a resolution of about 50 nm is obtained. By the ion beam B, not only are secondary electrons emitted from the surface 11a, but secondary electrons are also emitted from the surface vicinity somewhat inside the interior of the BOX layer 11 from the surface 11a; so that information of the surface 11a and of the surface vicinity as well are included in the SIM image.

Figure 2C:
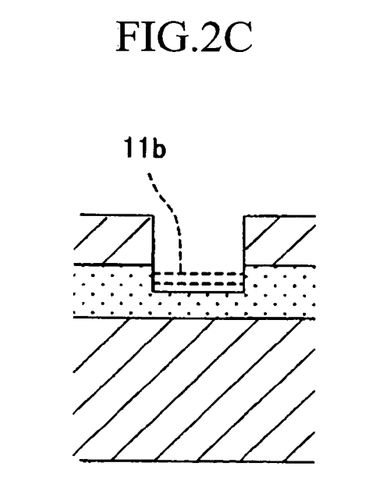
FIG. 2C is an explanatory figure schematically showing a situation during inspection of a sample.
Figure 2D:
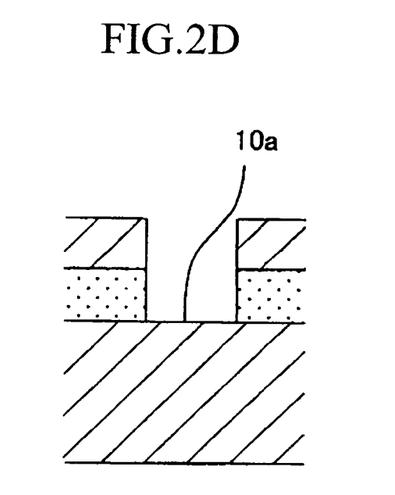
FIG. 2D is an explanatory figure schematically showing a situation during inspection of a sample.

Next, as shown in FIG. 2C, along with etching the surface 11b of the BOX layer 11 which has been etched with the ion beam B, the secondary electrons are detected, and a SIM image of the surface 11b is imaged. And, as shown in FIG. 2D, SIM images of each of the surfaces of the BOX layer which have been etched are successively accumulated, until the surface 10a of the silicon substrate 10 is exposed.

Figure 3:
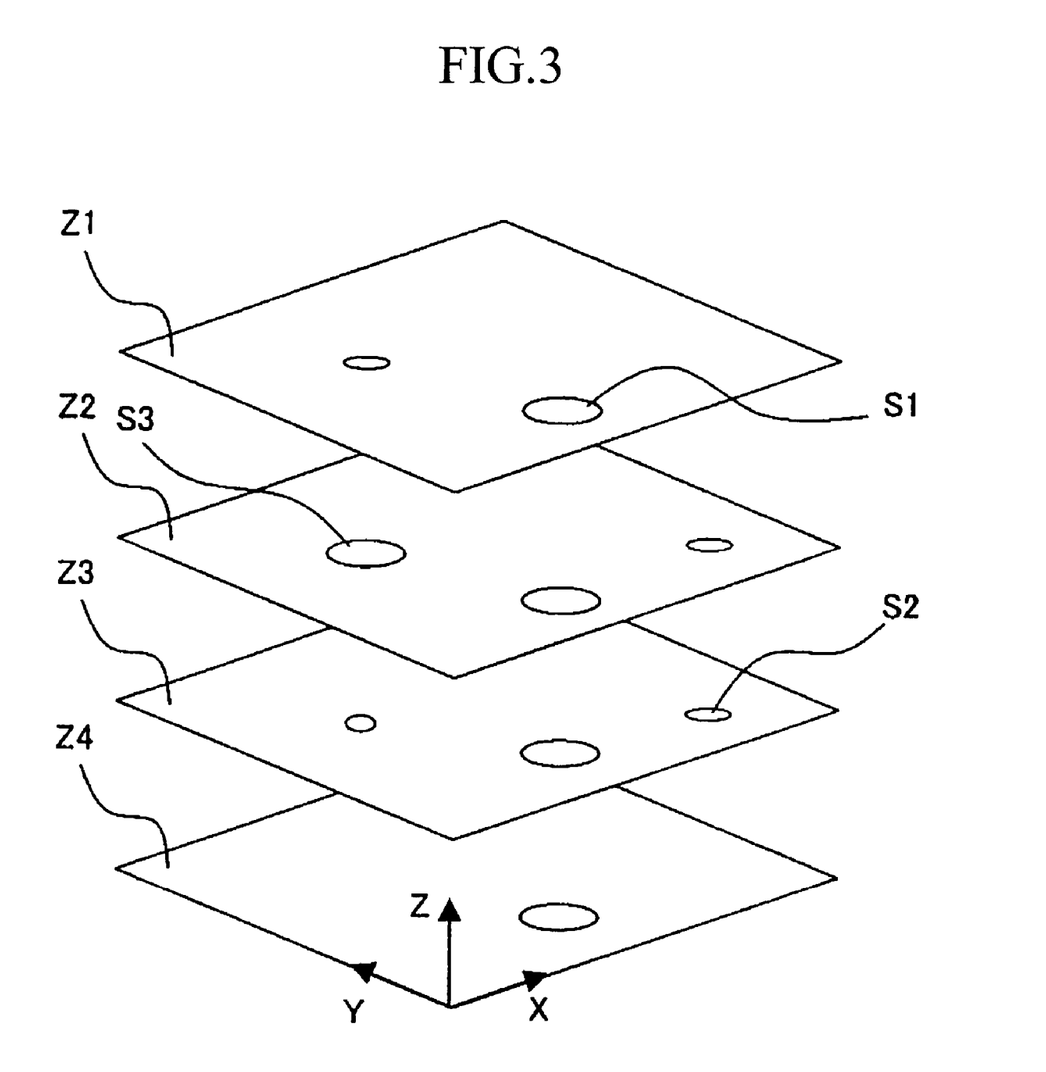
FIG. 3 is a schematic figure of a quasi three dimensional inspection result.

By this inspection method of the substrate sample 2, SIM images Z1 through Z4 are obtained at various depth positions of the BOX layer 11, as shown schematically in FIG. 3.

For example, the SIM image Z1 (the X-Y plane) corresponds to the surface 11a, while the SIM image Z2 corresponds to the surface 11b, and, successively, they are accumulated intermittently in the thickness direction (the Z direction), to constitute the results of inspection. By this method, not only is it possible to measure the silicon islands penetrating along the Z direction (the silicon island image S1), but also it is possible to measure the silicon islands which are not exposed upon the surface 11a but are positioned in the interior of the BOX layer 11 (the silicon island image S2), and the silicon islands for which the size varies in the Z direction (the silicon island image S3). It is possible to enhance the accuracy of inspection, since the measurements are performed directly. It is possible to enhance the accuracy of the inspection information in the Z direction yet further, by reducing the etching amount and imaging SIM image at high frequency.

Since the etching and imaging of SIM image is performed by the FIB apparatus at the same time in the inspection, the inspection is performed with a single apparatus in a short time. It is also possible to obtain a more accurate result, since there is no requirement to move the substrate sample 2 between etching and imaging of the SIM image and the substrate sample 2 is regularly immobilized.

The inspection method, is effective in the case that the secondary electron emission level is largely different between the BOX layer 11 and the silicon islands, as for a SOI wafer as the substrate sample 2; and, in particular, it is suited to inspect a SIMOX wafer in which a large number of silicon islands are included.

Next, a manufacturing method of a piece for analysis using the above described inspection method will be explained using FIG. 4.

Figure 4A:
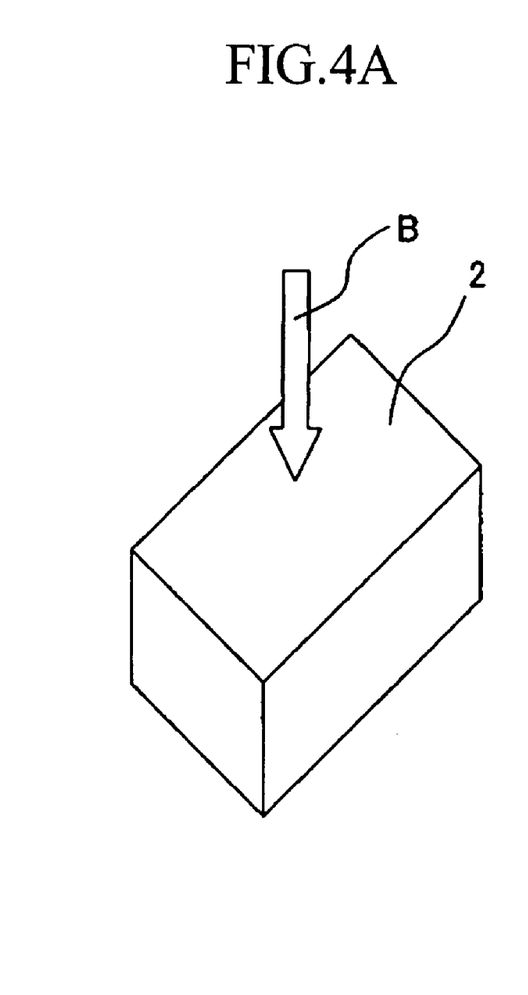
FIG. 4A is a schematic figure showing a situation when manufacturing a piece for analysis.
Figure 4B:
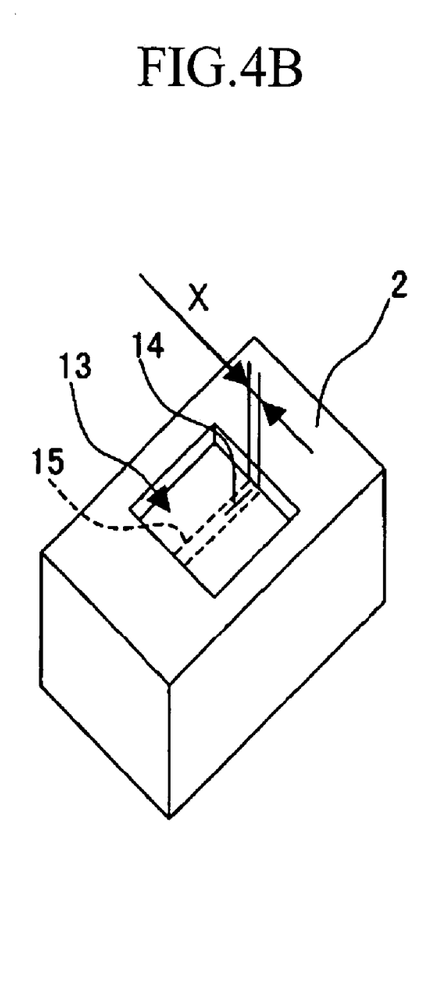
FIG. 4B is a schematic figure showing a situation of manufacturing a piece for analysis.

First, as shown in FIG. 4A, when inspecting the substrate sample 2 by irradiating an ion beam B from above upon the substrate sample 2, an inspection region 13 is etched, as shown in FIG. 4B. And the inspection region 13 is etched until a silicon island which constitutes the object of analysis is specified, and, when a silicon island is specified, a marking 14 is made upon its surface. Next, in order to manufacture a thin film 16 (an analysis region), a region 15 including the marked spot is specified to be of a constant thickness X, and the portions other than the region 15 are etched, so as to leave a thickness X not more than 0.5 μm. In other words, the portions of the substrate sample 2 positioned at the front and back sides of the thin layer 16 are removed by etching, so that the silicon island which has been specified remains within the thin film 16, and thereby a piece for analysis 17 is manufactured so that, as shown in FIG. 4C, the front and rear surfaces of the thin film 16 are exposed at both sides of the substrate sample 2.

By the manufacturing method of a piece for analysis, it is possible to manufacture a piece for analysis 17 in which a silicon island is reliably present in the thin film 16, and it is possible to enhance the efficiency of the analysis over the prior art. By this manufacturing method of a piece for analysis, it is possible to manufacture a piece for analysis at low cost, whereas the manufacturing cost was high in the prior art involving useless operations such as manufacture of a piece including no silicon island.

Figure 4C:
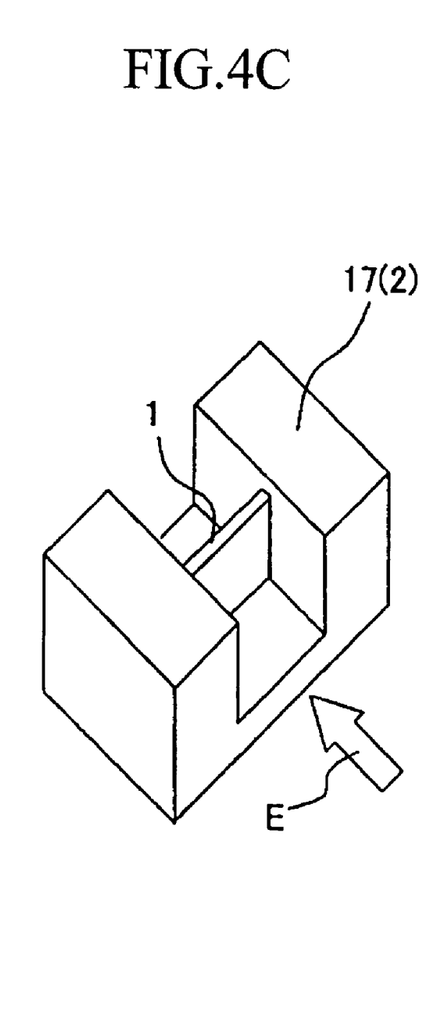
FIG. 4C is a schematic figure showing a situation of manufacturing a piece for analysis.
Figure 5A:
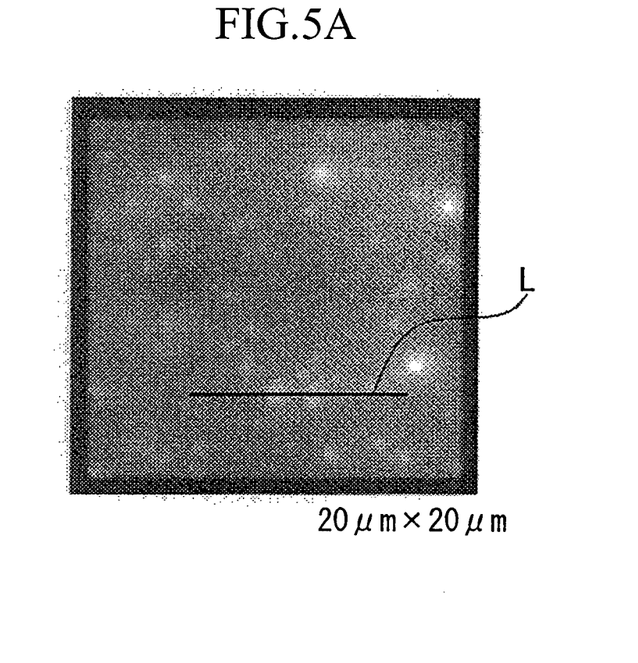
FIG. 5A is a SIM image of a substrate sample.
Figure 5B:
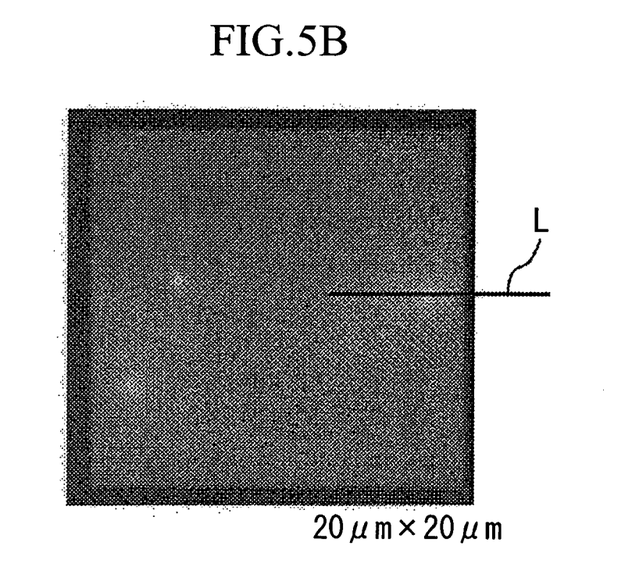
FIG. 5B is a SIM image of a substrate sample.
Figure 6A:
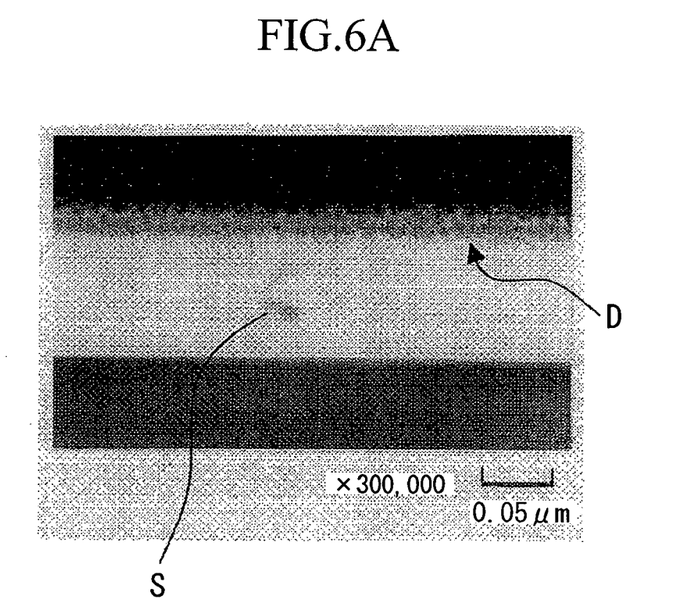
FIG. 6A is a TEM image of a section taking a line drawn in the SIM image shown in FIG. 5.
Figure 6B:
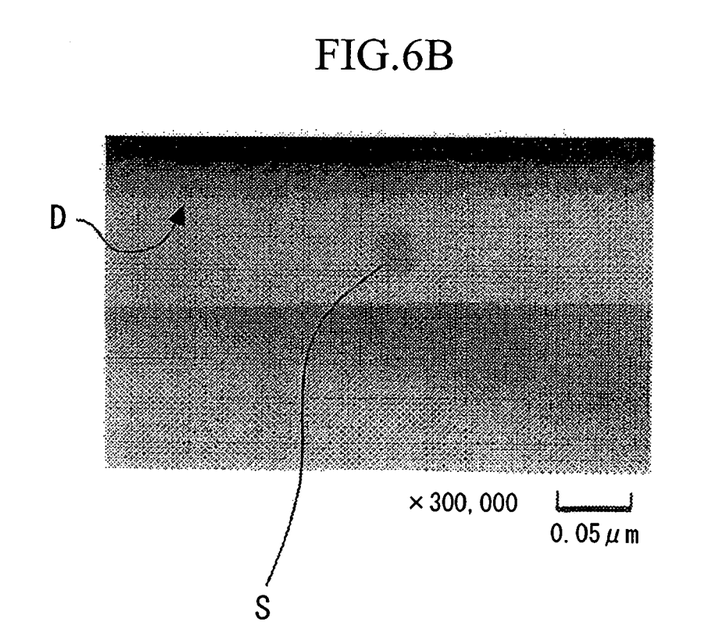
FIG. 6B is a c TEM image of a section taking a line drawn in the SIM image shown in FIG. 5.

The piece for analysis which has been manufactured in this manner is irradiated with electrons by TEM from the direction shown by the arrow sign E in FIG. 4C, and the silicon island within the thin layer 16 is imaged. SIM images of an etched substrate sample 2 are shown in FIG. 5A and FIG. 5B. FIG. 6A shows a TEM image at section taken along the line L appended to the SIM image of FIG. 5A, while in FIG. 6B a TEM image is shown which corresponds in the same way to FIG. 5B. Each of the sides in FIG. 5 is 20 μm, and the dark contrast in the SIM images is the BOX layer, while the bright contrast is the silicon islands. In FIG. 6, the scale shown at the lower right is 0.05 μm, and a silicon island S appears like a shadow in the BOX layer of bright contrast. In the TEM image of the piece for analysis made in this manner, as shown in FIGS. 6A and 6B, the damaged face D by etching is regularly imaged. And, by observing the TEM image, it is possible to analyze the shapes of the defects and the internal state, in other words the state such as the shape and the type of the silicon islands (single crystal or poly-crystal).

With the analyzing device 9, it is possible to analyze the three dimensional distribution of silicon islands from the SIM images obtained by the above described inspection method and have been accumulated. In the prior art, only the X-Y surface was analyzed from a SIM image, while by providing the analyzing device 9 to the FIB apparatus 1, it is possible to analyze the three dimensional distribution of the silicon islands by combining the data for the X-Y surfaces and the data for the Z direction, and it is possible to perform analysis of any desired cross section other than an X-Y surface.

It is possible to specify manufacturing conditions for the SOI wafer under which production of silicon islands can be suppressed, by feeding back the result of analysis of silicon islands based upon the state of each of the various silicon islands obtained from the TEM images, and the results of analysis based upon the three dimensional distribution of silicon islands obtained from the SIM images. For example, in the case of a SIMOX wafer, based upon the three dimensional distribution of the silicon islands, it is possible to specify conditions such as increase of the implantation energy, when increasing the amount of oxygen ion implantation to those spots tending to form a large number of silicon islands. By this method, it is possible to manufacture a SOI wafer in which only a small number of silicon islands is included within the embedded silicon oxide layer. A SOI wafer manufactured by this manufacturing method has high precision and high quality, and excels in various characteristics. It is also possible to enhance the yield of the SOI wafer manufacturing process.

It should be understood that although, in this embodiment, a SOI wafer was used as the substrate sample 2, and a BOX layer 11 was used as the insulating base material formed upon the substrate sample 2, as the base material for this inspection method, general insulating materials will be acceptable, such as a nitride, an oxide, or an organic macromolecule or the like; and, as the substrate sample 2, it is possible to inspect a substrate such as glass, ceramics, or an oxide semiconductor or the like. As a sample other than such substrate, it is possible to use a laser crystal, a SAW (surface elastic wave element), a photochromic glass, or a color filter including metallic nanoparticles, or the like, and it is possible to inspect the internal structure thereof. For the ion beam B, other than $Ga^+$, $O^+$, $Cs^+$, $Ar^+$, or the like may be used; as the means for imaging the secondary electrons, a SEM, a STEM, or a TEM may be used; and as the means for performing the etching, chemical etching may be used. Further, it is possible to measure the silicon islands in a satisfactory manner, provided that, in the FIB apparatus 1, the ion beam acceleration voltage is in the range of 15 to 40 keV, the ion beam current value is greater than or equal to 3.6 pA, and the ion beam diameter is greater than or equal to 18 nm.

EXAMPLE

In the following, examples related to the present invention will be explained. As an example, under the subsequently described conditions, after implanting oxygen into a silicon wafer, the silicon wafer was shifted into a heat processing oven, heated up to 1340° C. at a temperature elevation rate of 1° C. per minute in a temperature elevation process, kept at 1340° C. for ten hours in an oxidization process, and, after having been kept for five hours at 1340° C. in an annealing process, cooled to 600° C. at a cooling rate of 1° C. per minute in a temperature lowering process, whereby a SOI wafer was manufactured.

After the shift to the heat processing oven until the completion of the temperature lowering process at 600° C., except for the oxidization process, argon gas including oxygen at a partial pressure ratio of 4% was supplied to the heat processing oven at 25 slm. In the oxidization process, oxidization was performed by supplying argon gas including oxygen at a partial pressure ratio of 40% to the heat processing oven at 25 slm.

As a condition for oxygen ion implantation into the silicon wafer during the oxygen implantation process, the implantation energy was fixed as 163 eV, and the dosage of the oxygen ions was varied over the range of 1.75 to $2.50 \times 10^{17}$ atoms/$cm^2$.

By the inspection method of the above described embodiment, the density of Si islands in the BOX layer was measured from the SOI wafer, and based on the three dimensional distribution of the Si islands, the relationship between the dosage of the oxygen ions and the density of the Si islands. The results thereof are shown in FIG. 7.

Figure 8:
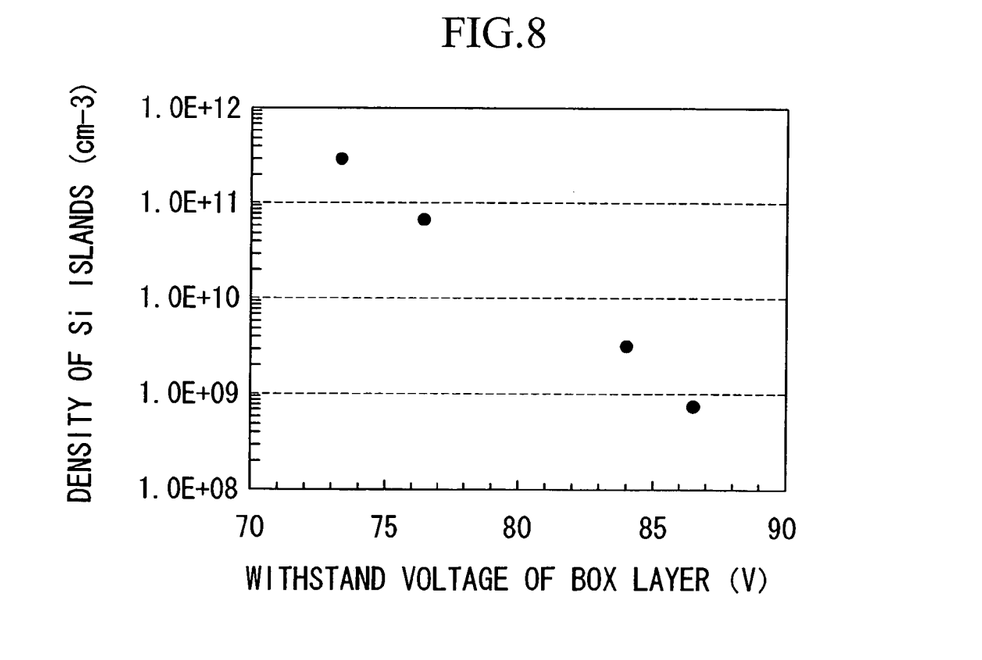
FIG. 8 is a graph showing the relationship between the defect density of a BOX layer and the withstand voltage of the BOX layer, in an example of the present invention.

At this time, the relationship between the defect density of the BOX layer and the withstand voltage of the BOX layer was analyzed. The results thereof are shown in FIG. 8.

Here, as the conditions for FIB measurement of the density of the Si islands in the BOX layer, the acceleration voltage was made to be 30 KeV, the probe current was made to be 1.3 nA, and the probe diameter was made to be 92 nm.

Figure 7:
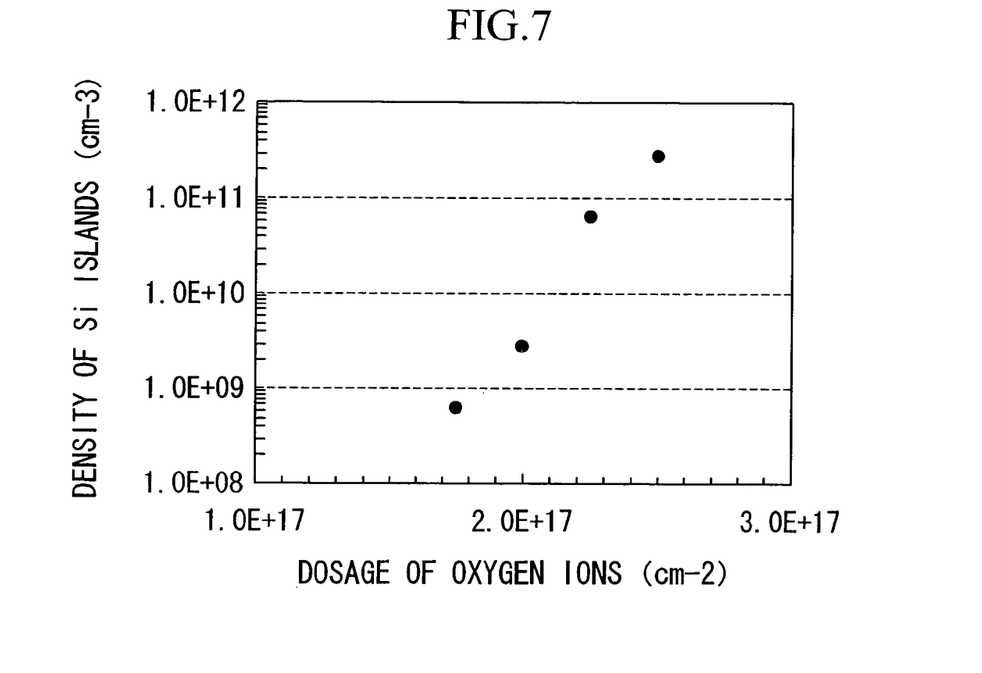
FIG. 7 is a graph showing the relationship between the dosage of oxygen ions and the density of Si islands in a BOX layer, in an example of the present invention.

As is clear from the results in FIG. 7, since the density of the Si islands in the BOX layer became high under the large dosage of the oxygen ions, the production of the Si islands in the BOX layer is suppressed when the dosage of the oxygen ions is as low as possible.

At the same time, the thickness of the BOX layer is not formed with uniform thickness when the dosage of the oxygen ions is lower than $1.70 \times 10^{17}$ atoms/$cm^2$, and furthermore, when the dosage is lower than $1.50 \times 10^{17}$ atoms/$cm^2$, then portions were produced in which the BOX layer was not formed in the direction within the surface of the wafer. Since the thickness of the BOX layer is not uniform under the above condition, it is appropriate to specify the dosage of the oxygen ions to the neighborhood of $1.75 \times 10^{17}$ atoms/$cm^2$ as a process condition. It is possible to manufacture the SOI wafer by feeding back the manufacturing condition specified by this result that the dosage for the oxygen ions in the oxygen implantation process should be set to around $1.75 \times 10^{17}$ atoms/$cm^2$.

Furthermore, as is clear from the results of FIG. 8, a SOI wafer manufactured by feeding back the aforementioned manufacturing condition specified to around $1.75 \times 10^{17}$ atoms/$cm^2$ have a high withstand voltage in the BOX layer, and also have a satisfactory quality.

When the dosage of the oxygen ions is decreased within the range of 1.75 to $2.50 \times 10^{17}$ atoms/$cm^2$, the size of the Si islands has a tendency to decrease with the decreasing oxygen dosage and it becomes difficult for insulation breakdown to occur. Therefore, a SOI wafer manufactured under these manufacturing conditions has a satisfactory quality.

INDUSTRIAL APPLICABILITY

As has been explained above, according to the inspection method of the invention, it is possible to measure the conductive materials within the base material directly, since ions or electrons are irradiated upon the surface of the inspection region of the base material, the secondary electrons emitted from the surface and the vicinity of the surface are imaged, and, successively, while etching the inspection region, the secondary electrons emitted from the etched surface and the vicinity of the surface are imaged, and the conductive materials within the base material are measured based on the accumulated surface images, and the internal state of the sample is inspected. By this method, it is possible to inspect the internal state of the sample accurately in a three dimensional manner.

The invention claimed is:

1. An inspection method for inspecting an internal state of a silicon on insulator (SOI) wafer by measuring silicon islands within an insulating base material of a silicon oxide film formed in the SOI wafer, the method comprising:
   irradiating ions or electrons upon the surface of the inspection region of said silicon oxide film;
   imaging a surface image of secondary electrons emitted from said surface and from its vicinity;
   etching said inspection region;
   imaging a surface image successively with secondary electrons emitted from an underlying surface and from its vicinity, renewed successively at the etched depth;
   measuring said silicon islands within said silicon oxide film based upon accumulated said surface images; and
   inspecting the internal state of said SOI wafer,
   wherein said etching is performed with an ion-beam having an acceleration voltage of 15 to 40 keV, beam current greater than or equal to 3.6 pA, and beam diameter greater than or equal to 18 nm, and
   wherein said etching and said imaging of said surface image are performed at the same time.

2. The inspection method according to claim 1, wherein said SOI wafer is manufactured by the SIMOX technology.

3. A manufacturing method of a piece for analysis using the inspection method according to claim 1, wherein
   said silicon islands within said silicon oxide film are specified based upon said surface image;
   said base material is etched away, other than a thin film of an analysis region, leaving said silicon oxide film in the depth direction which constitutes said analysis region, so that said analysis region is formed including at least a portion of specified said silicon islands; and
   thereby a piece for analysis having said analysis region is manufactured.

4. An analysis method using a piece for analysis manufactured by the manufacturing method of a piece for analysis according to claim 3, wherein
   the state of said silicon islands is analyzed based on the observation of said conductive material include is said piece for analysis.

5. A manufacturing method of a SOI wafer using an analysis method according to claim 4, wherein
   said SOI wafer is manufactured under manufacturing conditions specified by feeding back the state of said silicon islands or its three dimensional distribution which has been analyzed.

6. An analysis method using an inspection method according to claim 1, wherein
   the three dimensional distribution of said silicon islands is analyzed from accumulated said surface images.

7. An analyzer used in the analysis method according to claim 6, comprising:
   a stage upon which said SOI wafer is mounted;
   an ion source producing an ion beam having an acceleration voltage of 15 to 40 keV and beam current if greater than or equal to 3.6 pA, which is irradiated upon said SOI wafer;
   a beam control device for focusing and scanning the ion beam;
   a secondary electron detector which detects secondary electrons emitted from said SOI wafer;
   a control system which controls the ion source and the beam control device;
   a imaging system which images the result of detection by said secondary electron detector as said surface image; and
   an analyzing device which analyzes the three dimensional distribution of said conductive material from accumulated said surface images.

* * * * *